United States Patent [19]

Rosenshein

[11] Patent Number: 5,409,473
[45] Date of Patent: Apr. 25, 1995

[54] URINARY COLLECTION DEVICE

[76] Inventor: Beth B. Rosenshein, 7770 Youngdale Way, Unit-E, Stanton, Calif. 90680

[21] Appl. No.: 69,183

[22] Filed: May 28, 1993

[51] Int. Cl.[6] .................................................. A61F 5/44
[52] U.S. Cl. ..................................... 604/329; 128/761
[58] Field of Search ................ 604/326, 329; 128/761, 128/762, 767; 4/144.1–144.4

[56] References Cited

U.S. PATENT DOCUMENTS

| | | | |
|---|---|---|---|
| 3,499,327 | 3/1970 | Lane, Jr. | 128/762 |
| 3,625,654 | 12/1971 | Van Duyne | 4/144.2 |
| 4,492,258 | 1/1985 | Lichenstein et al. | 141/1 |
| 4,569,090 | 2/1986 | Muller | 4/144.2 |
| 4,696,067 | 9/1987 | Woodward | 4/144.3 |
| 4,852,560 | 8/1989 | Hermann | 128/762 |

*Primary Examiner*—Jerome L. Kruter
*Attorney, Agent, or Firm*—Herbert M. Shapiro

[57] ABSTRACT

An inexpensive, disposable device for collecting a midstream urine specimen from a female donor which device can be used by the donor herself without professional help. The device comprises a container having two chambers, one for collecting and discarding the initial, unwanted portion of the urine flow and the other chamber for collecting and retaining the later, cleaner, portion of the urine flow. A pivoted "paddle" valve comprising two conjoined paddles is disposed between the chambers and—controlled by the flow of urine, itself—directs the first, contaminated, portion of the urine to the discard chamber and directs the remainder of the flow to the specimen chamber. Initially, one of the paddles covers and seals the specimen chamber to prevent urine from entering that chamber. The other paddle is suspended over the opening of the discard chamber. As the flow of urine begins, the paddle suspended over the discard chamber in the path of the flow of urine is pushed downward by the force of the leading flow of urine. The downward motion of the discard paddle causes the valve to turn like a paddle wheel. As the valve rotates, the paddle initially disposed over and covering the specimen chamber opens that chamber and continues rotating until it intersects and is stopped by the wall of the discard chamber. Thus, the paddle which initially closed the specimen chamber turns and closes the opening to the discard chamber and at the same time redirects the flow of urine into the specimen chamber. In short, the initial flow of urine striking the paddle over the discard chamber is collected in the discard chamber. At the same time this initial flow turns the valve, opening the specimen chamber and closing the discard chamber thereby directing the subsequent cleaner urine flow to the specimen chamber.

6 Claims, 2 Drawing Sheets

URINARY COLLECTION DEVICE

BACKGROUND OF THE INVENTION

1. Field of the Invention

This invention relates to urine specimen collecting means and more particularly to an inexpensive, simple-to-use, disposable device for collecting the mid-stream portion of urine from a female donor.

2. Description of the Prior Art

Urine analysis is a simple and useful tool in diagnosing urinary tract infections which are more common in women. The usefulness of urine analysis for the detection and identification of these infections is lessened by the difficulty in obtaining a specimen which has not been contaminated by the bacteria on, and secretions from, the tissues past which the urine flows before being collected. As urination begins, the flow tends to be weaker. This weaker flow contacts more tissue area and picks up and carries with it more secretions and bacteria. The later, mid-stream flow, exits the body faster and with more force and is therefore fleer of contaminating bacteria and secretions. In addition, the initial, slower, flow serves to "clean" the tissues past which it flows, further causing the mid-stream flow to be less contaminated. Thus, in collecting urine specimens for purposes of diagnosis, it is more advantageous to collect mid-stream urine which is fleer of contaminating bacteria and secretions.

The simplest method for collecting a mid-stream urine specimen is to allow the urine flow to begin, wait a period of time and insert a collecting container into the path of the urine flow. Since it is difficult to stop the flow after it has begun, it is also difficult to catch the mid-stream sample without soiling the hands and the outside of the container. In addition, the individual, herself, must make a judgment as to the correct point at which to place the collector into the flow, thereby introducing anxiety and risk of contamination from errors in judgment by someone who is very likely to be unfamiliar with the procedure. Other means for separating and collecting the mid-stream flow include devices having separate chambers for example, as described in U.S. Pat. No. 3,722,503 whereby the contents of one chamber overflow to a second chamber when a specified volume is attained. In a different arrangement (U.S. Pat. No. 4,569,090), the mouth of a collection bottle protrudes into a larger container. The first portion of the urine is collected in the larger container. When the level of the urine reaches the mouth of the bottle, the urine enters the bottle. These prior art arrangements do not actually provide for the separation of the initial-stream and mid-stream flows. Thus, a portion of the initial flow may be mixed, perhaps because of turbulence, with the mid-stream flow as the level of the urine reaches an overflow level as described in the prior art or as in the case of U.S. Pat. No. 4,569,090 cited above, reaches the mouth of the collection jar.

The patent literature also describes devices, in other context, which employ valve-like devices in urine collection embodiments. The primary purpose of those valves is to prevent spillage after the urine is collected and prior to its being destroyed. For example, U.S. Pat Nos. 3,356,218 and 4,457,314 disclose valve-like devices in two different types of urine collectors. The valve in U.S. Pat. No. 4,457,314 is described as an "anti-back flow mechanism" employed primarily to prevent spillage of the contents. Other U.S. patents that disclose one-way type valves for the purpose of preventing spillage include: U.S. Pat. Nos. 3,928,875; 4,095,124; 4,586,041 and 4,734,154.

Another class of valve urine collectors involve those designed to collect mid-stream urine samples. For example, U.S. Pat. No. 4,494,581 discloses a mid-stream urine collection device which describes, in FIG. 7 thereof, a mechanism in which a floating cork closes a valve after an initial sample of urine has been obtained so that the remaining specimen to be collected will be from the mid-stream.

SUMMARY OF THE INVENTION

The urine collection device of the present invention is inexpensive, highly convenient and almost intuitively obvious in the manner of its use, thereby eliminating the need for involved explanations or professional assistance. Broadly speaking, the arrangement of the present invention comprises a two-chambered, beaker-like container with a conveniently shaped and relatively long handle. The cross-sectional shape of the pitcher is, in one embodiment, an oblong. Although the dimensions themselves are not critical to the invention, the dimensions of the pitcher should be selected for convenient and comfortable collection of urine flow even from a female standing upright. In addition, the chambers of the pitcher must be large enough to hold virtually all the urine flow during a single micturition. In accordance with one embodiment of the present invention, the oblong cavity of the pitcher is divided by a wall into two chambers, a discard chamber and a specimen chamber. Situated between the two chambers and over the dividing wall is a valve which operates like a paddle wheel. Before urine enters the container, one of the paddles of the valve covers the opening of the specimen chamber while the second paddle is disposed over the opening of the discard chamber and in the flow of urine. The paddles are rigidly attached at right angles to one another. In the illustrative embodiment, as urine strikes the paddle over the discard chamber, the paddle is forced downward. As it is forced downward, the paddle covering the specimen is pivoted around, opening the specimen chamber. As the paddle covering the specimen chamber rotates, it is stopped by the wall of the discard chamber, thereby closing the discard chamber and directing urine flow to the specimen chamber.

One of the chambers, which may be smaller than the other, collects the first portion of the urine flow and has a stoppable exit aperture or hole situated near the bottom of the pitcher on the short side of the oblong of the pitcher. Thus, the pitcher may be held over a toilet during collection and the unwanted urine in the discard chamber simply channeled through the aperture to the toilet. The aperture may be raised a short distance from the floor of the pitcher, to avoid dripping urine when the pitcher is removed from the area of the toilet so that the usable specimen may be taken for testing. Alternatively, if a stopper is used, the stopper may be kept in the aperture until it is convenient to remove the stopper and dispose of the unwanted portion of the urine. The handle is attached to the beaker on the short wall of the discard chamber to permit the user to easily position the aperture, if appropriate, over a toilet.

The handle initially extends up and away from the pitcher, flattens out and then turns down. The purpose of the length and angle of the handle is to permit the user to hold the pitcher below the body and in the stream of the urine while keeping the hand well away from the flow. The user may position herself over a toilet and place the opening of the pitcher between her legs in such a way as to collect all the urine eliminated. The leading portion of the flow of the urine is prevented from entering the specimen chamber by the specimen paddle of the paddle wheel valve. At the same tinge, the leading edge of the flow pushes the discard paddle of the paddle wheel valve down. The leading portion of the urine impacts the discard paddle and flows into the discard chamber and out the hole in the bottom of the discard chamber. As the discard paddle is forced down by the leading portion of the urine flow, the specimen paddle of the paddle wheel valve, rotates around to close the opening of the discard chamber and redirect the path of the urine into the specimen chamber.

The inherent advantages and improvements of the present invention will become more readily apparent upon reference to the following detailed description of the invention and by reference to the accompanying drawings.

DETAILED DESCRIPTION OF THE INVENTION

During the course of this description, like numbers will be used to identify like elements according to the different figures which illustrate the invention.

Figure 1:
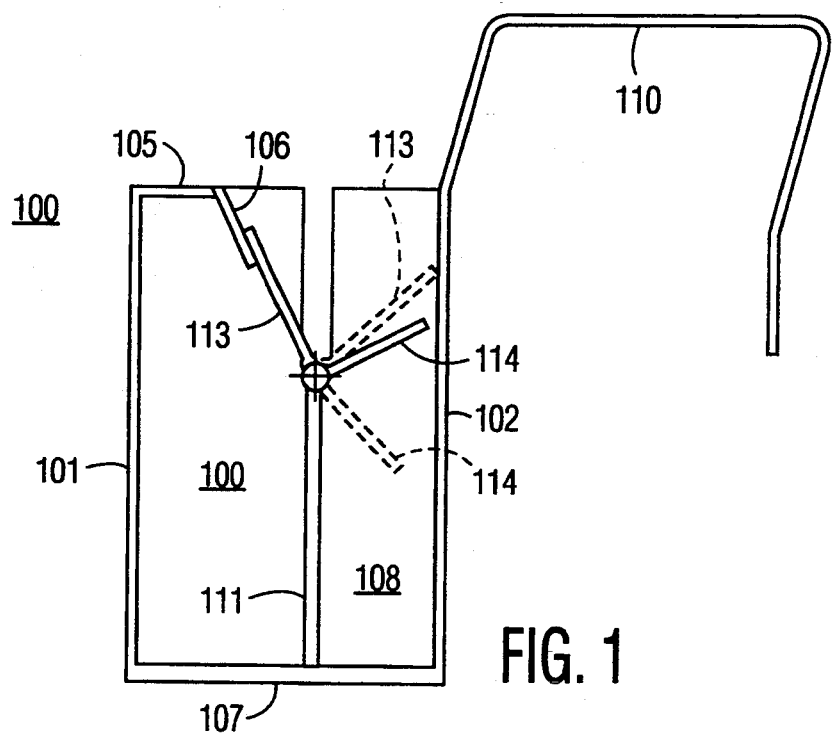
FIG. 1 is a cross-sectional view of a urine specimen collection device made in accordance with the present invention.
Figure 2:
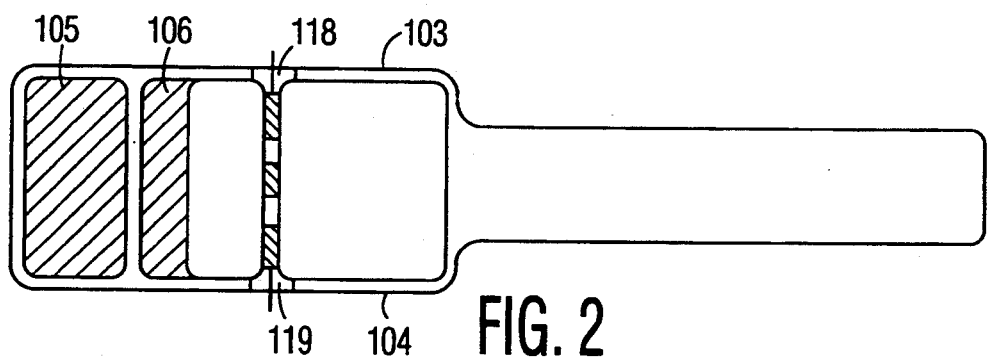
FIG. 2 is a top elevation view of the urine specimen collection device.

Referring to FIGS. 1 and 2, there is illustrated a urine specimen collector in accordance with the present invention and indicated generally as 100. This device consists of an oblong beaker comprising vertical walls 101, 102, 103, and 104, top closure 105, top closure stop extension 106 and base 107. Referring to FIG. 2, in particular, it is seen that top closure 105 extends partially over specimen chamber 109 and ends in downwardly extending stop extension 106.

Handle 110, attached to wall 102, is shaped to permit the beaker to be conveniently held by a user beneath the trunk of the user's body during micturition.

In the embodiment shown in the drawings, handle 110 initially extends upward and away from the beaker, then extends out roughly perpendicular to wall 102 and finally turns downward. A handle one-half or three-quarters the width of the beaker may provide good leverage for a user, paricularly one who is standing during urination.

Divider wall 111 within the cavity of the beaker extends vertically upward from base 107 and extends between walls 103 and 104 forming two separate chambers: discard chamber 108 and specimen chamber 109. The upper rim of divider wall 111 is conveniently semicircular in shape.

Figure 3:
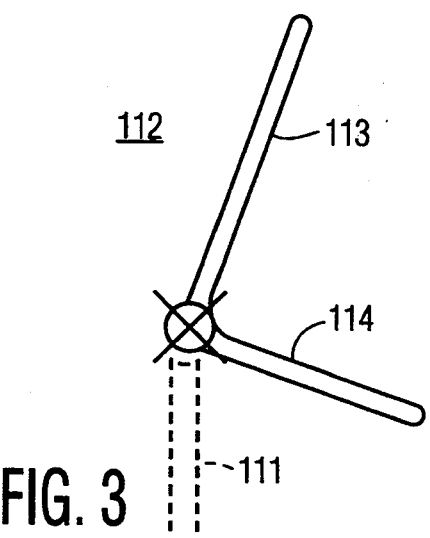
FIG. 3 is a cross-sectional view of the paddle valve.
Figure 4:
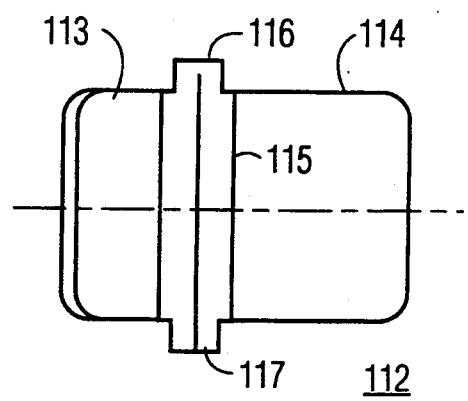
FIG. 4 is a top elevation of the paddle valve.

FIG. 3 shows paddle valve 112 in cross-sectional view and FIG. 4 shows the valve in top elevation. In the embodiment of the invention described herein, paddle 113 and paddle 114 are rigidly connected at right angles to one another along the pivoting cylinder 115. Although the paddles are shown configured to be at fight angles to one another the angle is illustrative only. Another angle may be as effective. Along the axis of intersection of paddles 113 and 114 is pivoting cylinder 115. The fight circular cylindrical shape of pivoting cylinder 115 permits the valve to rotate about the long axis of the intersection of paddles 113 and 114. The radius of pivoting cylinder 115 of paddle valve 112 is conveniently the same as the radius of curvature of the semicircular shape of the rim of divider wall 111. Thus, pivoting cylinder 115 of paddle valve 112 in the illustrative embodiment is configured to be seated in the semicircular groove along the rim of divider wall 111 so that when seated, paddle 112 may be rotated around the axis of pivoting cylinder 115.

FIG. 4, which is a top elevation view of paddle valve 112, is useful to a further understanding of the principles of the present invention. In particular, it can be can seen from FIG. 4 that pivoting cylinder 115 is longer than and therefore extends beyond the width of paddles 113 and 114 forming cylinder extensions 116and 117. Extensions 116and 117 are intended to fit into slots in the internal surfaces of the walls of specimen collector 100 such that paddle valve 112 may rotate about the axis of pivoting cylinder 115 but be otherwise held in position within the cavity of the container.

Referring to FIG. 2, in order to insert paddle valve 112 into the cavity of the beaker and position it along the rim of divider wall 111 slots 118 and 119 are shown niched in the internal surfaces of walls 103 and 104, respectively. The width of slots 118 and 119 is the same as the diameter of pivoting cylinder 115 extensions 116 and 117 with sufficient tolerance to permit the extensions to slide down the slots. The base of each of slots 118 and 119 is formed in the shape of a half circle of the same radius as that of pivoting cylinder extensions 116 and 117 with sufficient tolerance to permit pivoting cylinder 115 to rotate freely in the bases of slots 118 and 119.

As is illustrated in FIG. 1, pivoting cylinder 115 of paddle valve 112, is seated in the grooved rim of divider wall 111. Paddles 113 and 114 are shown in solid line representation in the initial position prior to the beginning of micturition. In this position, paddle 113 rests against stop extension 106 thereby closing specimen chamber 109. At the same time, paddle 114 is suspended over discard chamber 108. As micturition begins, paddle 114 is driven downward by the force of the urine. As paddle 114 moves downward, paddle 113 rotates clockwise opening specimen chamber 109 and continues rotating until it intersects wall 102 of collector 100. In this position, paddle 113 directs the remaining flow of urine into specimen chamber 109. The position of paddles 113 and 114 after urination has begun (and paddle valve 112 has turned) is shown in broken-line representation on FIG. 1. The length of paddle 113 must be less than the distance between divider wall 111 and wall 102 in order to turn fully past the wall. Correspondingly, the length of paddle 113 must be long enough to rest firmly against stop extension 106 in the pre-micturition state and long enough to intersect wall 102 over discard chamber 108 to channel remaining urine into specimen chamber 109 after micturition has begun.

As will be apparent to those skilled in the art, the relative weights of paddles 113 and 114 must be defined to permit paddle 113 to rest against stop extension 106 while paddle 114 is suspended above discard chamber 108 before micturition begins. Correspondingly, the relative weights of paddles 113 and 114 must be such that the force from the flow of urine will be sufficient to exceed the opposing force exerted by paddle 113 leaning against stop extension 106.

Figure 5:
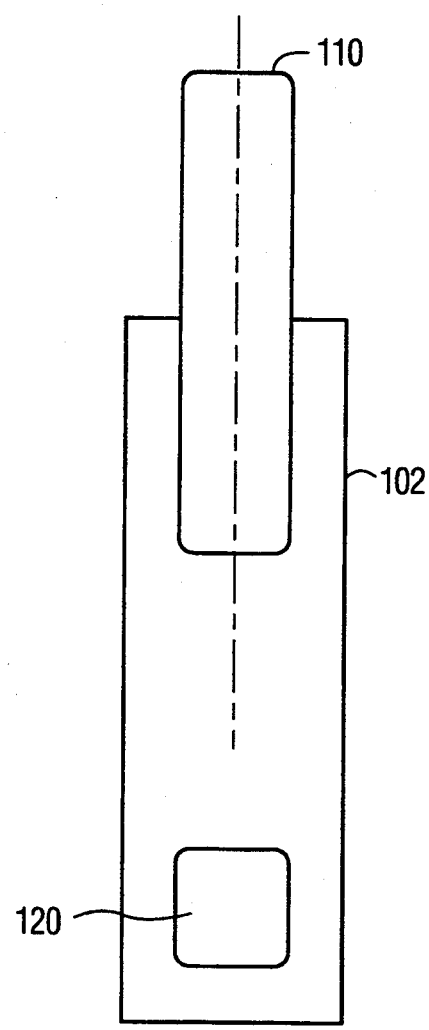
FIG. 5 is a side view of the collection device of the present invention showing the handle and the stoppable aperture.

FIG. 5 is an end view of collector 100 showing wall 102. In one embodiment of the present invention, an aperture 120 is cut in wall 102. Aperture 120 permits urine to be directed from discard chamber 108 directly to a toilet. That is, if collector 100 were used by a woman standing over a toilet, the initial flow of urine will flow through chamber 108 and aperture 120 and into the toilet for disposal. Aperture 120 may be raised slightly above the floor of discard chamber 108 to prevent unwanted dripping. A cap (not shown) may be provided to permit collector 100 to be used either to funnel urine to a toilet or to retain the discard urine for later disposal.

Although certain preferred embodiments of the invention have hereinbefore been described, it will be appreciated that variations of the invention will be perceived by those skilled in the art, which variations are nevertheless within the scope of this invention as defined by the claims appended hereto.

What is claimed is:

1. Apparatus for obtaining a relatively uncontaminated urine specimen comprising a collection beaker including a divider wall for separating the cavity of said beaker into a discard chamber and a specimen chamber, and valve means comprising first and second paddles rigidly conjoined along a pivoting axis, said valve means being disposed between said divider wall and the top of said beaker and further disposed to communicate with said discard and specimen chambers, wherein said paddles are arranged to be driven by the force of the flow of urine to turn about their pivoting axis thereby to direct the first portion of said urine specimen to said discard chamber and the remainder of said urine specimen to said specimen chamber, said beaker including a stop communicating with said valve for maintaining said valve in an initial position to collect urine between said paddles.

2. Apparatus as in claim 1 wherein said first and second paddles are of first and second different lengths, said first paddle being shorter than said second paddle.

3. Apparatus as in claim 2 wherein said collector further comprises a stoppable aperture near the base of said collector to permit urine collected in said discard chamber to be discarded.

4. Apparatus as in claim 3 further comprising a handle secured to the uppermost portion of said collector whereby said collector may be held by said handle in an upright position said handle further arranged to permit urine to be directed safely and cleanly to a disposal sink through said stoppable aperture.

5. A mid-stream urine collection device having a discard chamber for collecting the earlier portion of the urine flow and a specimen chamber for collecting the later portion of urine flow consisting of a rotatable nonspring loaded paddle wheel valve communicating with both of said chambers for rotating in response to the flow of said urine for directing the first portion of said urine to said discard chamber and for directing the second portion of said flow to said specimen chamber, said paddle wheel valve consisting of first and second paddles in fixed angular relationship to one another, one of said paddles being initially positioned over said discard chamber and one of said paddles being initially positioned over said specimen chamber, said device including a downward exstending stop member for initially positioning said valve paddles for collecting said earlier portion between said paddles.

6. Apparatus as in claim 5 wherein said first and second paddles are of first and second lengths, said first paddle being shorter than said second paddle.

* * * * *